United States Patent
Koros et al.

[11] Patent Number: 5,928,139
[45] Date of Patent: Jul. 27, 1999

[54] RETRACTOR WITH ADJUSTABLE LENGTH BLADES AND LIGHT PIPE GUIDES

[76] Inventors: Tibor B. Koros; Gabriel J. Koros, both of 610 Flinn Ave., Moorpark, Calif. 93021

[21] Appl. No.: 09/112,024

[22] Filed: Jul. 8, 1998

Related U.S. Application Data

[63] Continuation-in-part of application No. 09/066,078, Apr. 24, 1998, abandoned.

[51] Int. Cl.$^6$ .................................................. A61B 17/00
[52] U.S. Cl. ......................... 600/205; 600/215; 600/232; 600/235; 600/245; 600/213
[58] Field of Search .................................. 600/201, 205, 600/215, 232, 233, 235, 210, 213, 245, 219

[56] References Cited

U.S. PATENT DOCUMENTS

| | | | |
|---|---|---|---|
| 1,157,202 | 10/1915 | Bates et al. | 600/215 X |
| 1,706,500 | 3/1929 | Smith | 600/232 |
| 2,474,857 | 7/1949 | Newman | 600/215 X |
| 3,626,471 | 12/1971 | Florin | 600/205 |
| 3,965,890 | 6/1976 | Gauthier | 600/215 |
| 4,156,424 | 5/1979 | Burgin | 600/213 |
| 4,616,635 | 10/1986 | Casper et al. | 600/215 |
| 4,852,552 | 8/1989 | Chaux | 600/232 |
| 5,027,793 | 7/1991 | Engelhardt et al. | 600/210 |
| 5,728,046 | 3/1998 | Mayer et al. | 600/215 X |
| 5,788,630 | 8/1998 | Furnish | 600/232 |
| 5,795,291 | 8/1998 | Koros et al. | 600/213 X |

*Primary Examiner*—Jeffrey A. Smith
*Attorney, Agent, or Firm*—David O'Reilly

[57] ABSTRACT

Variable length blades for use with a retractor or distractor include a fixed upper portion and an adjustable extension that allows adjustment to accommodate a wide range of patients. A variable length retractor blade has a fixed upper portion that can vary in length from 10 to 15 cm. having a telescoping extension that can be adjusted to vary the length of the blade from 12 to as much as 24 cm. The variable blades include conventional flanges with a header for securing the variable blades on the end of retractor/distractor arms. An additional option is the inclusion of tubular guides in the variable length blade extension for placement of plurality of fixation screws and a light pipe to provide intensive illumination for the surgical site. Three tubular guides are provided in the upper and lower ends of the telescoping extension on the variable length blade for use with a distractor. The two outer tubular guides are used to place two fixation grooves in each blade to provide a stable platform for a distractor frame. A center tubular guide is used to position a light pipe for intense illumination of a surgical site.

26 Claims, 4 Drawing Sheets

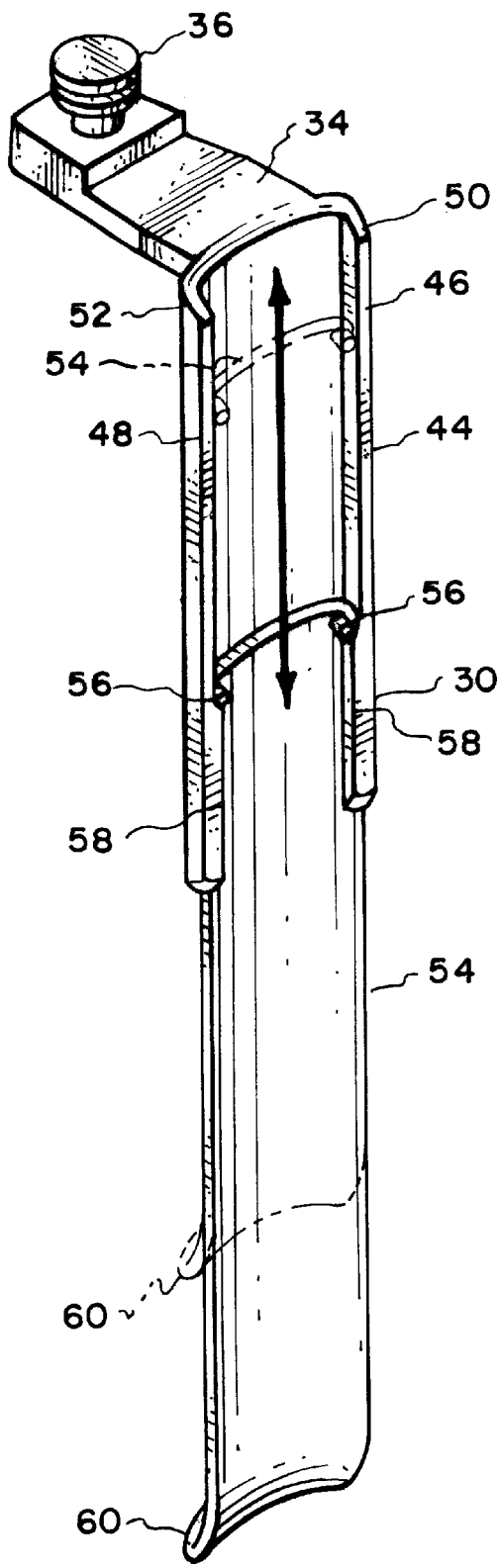
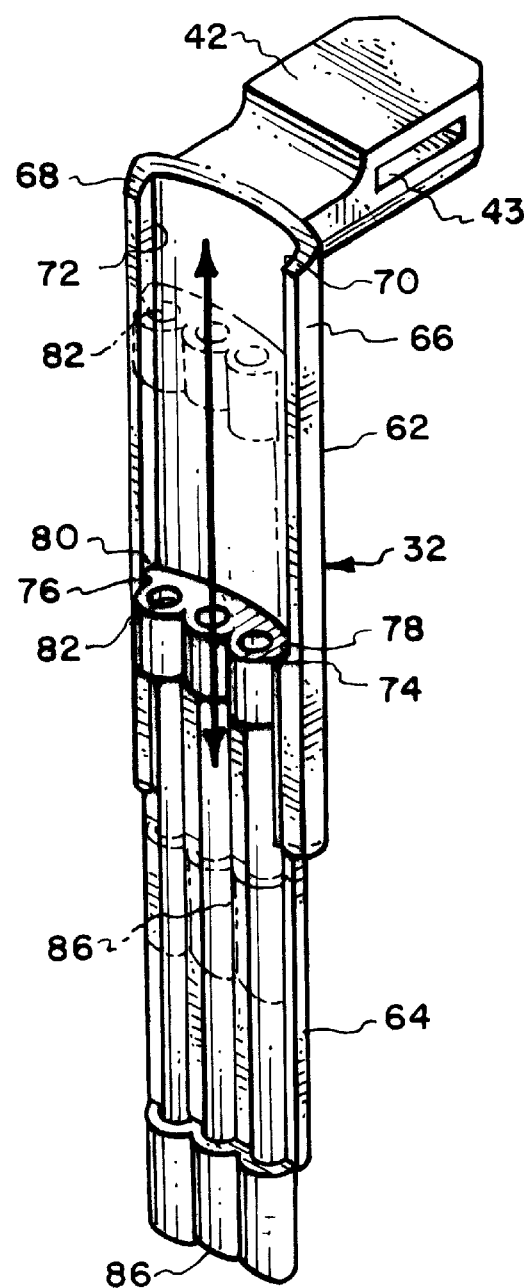
Fig. 2.
Fig. 3.

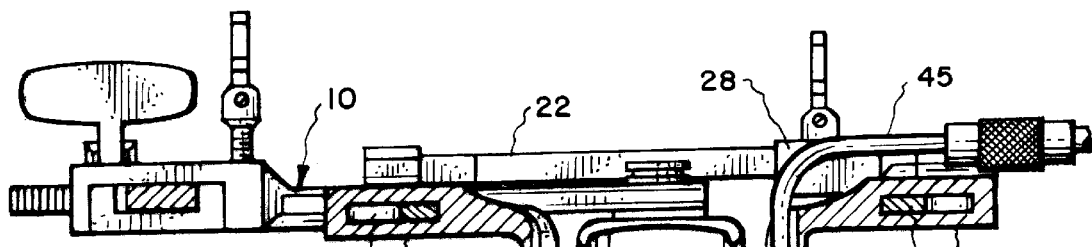
Fig. 5.
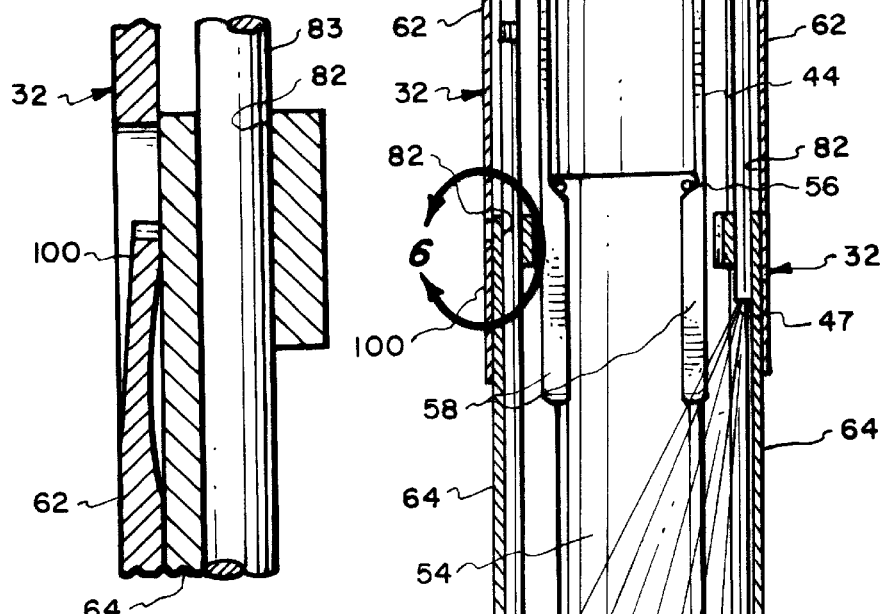
Fig. 6.
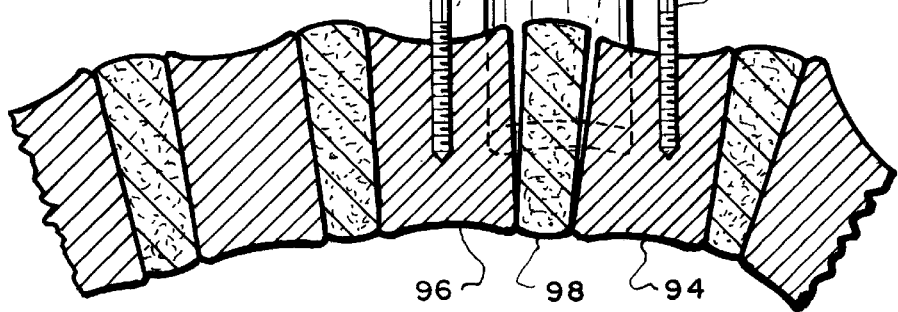

RETRACTOR WITH ADJUSTABLE LENGTH BLADES AND LIGHT PIPE GUIDES

CROSS-REFERENCE TO RELATED APPLICATIONS

This application is a Continuation-In-Part of applicants' patent application Ser. No. 09/066,078 filed Apr. 24, 1998 (now abandoned).

BACKGROUND OF THE INVENTION

1. Field of the Invention

This invention relates to retractors used in surgical procedures and more particularly relates to a retractor for lumbar spinal fusion that includes adjustable length retractor blades and guides for positioning fixation screws and a light pipe.

2. Background Information

In a surgical procedures trauma to the patient and damage to the tissue needs to be minimized as much as possible. To achieve this result surgeons try to keep incisions as small as possible when performing surgical procedures such as lumbar spinal fusions by making a midline mini-incision. However, it is necessary that the surgeon performing the delicate surgery to have a clear view of the operating field. A variety of retractors are available to keep an incision open and provide a clear view of the field of the operation.

Such surgical retractors are particularly important in performing spinal fusions, and particularly lumbar disc operations where the surgical procedure is provided by an anterior/lateral approach through the abdomen. One such retractor is disclosed and described in U.S. patent application Ser. No. 08/935,761 of T. Koros et al filed Sep. 23, 1997 and incorporated herein by reference. This application discloses a retractor in which the surgeon makes a small incision in the abdomen to view the region of the vertebrae where the lumbar disc operation is to be performed. The retractor disclosed is inserted in the incision to hold organs, muscles, arteries and other tissue out of the way and provide a clear view of the spinal region being operated on.

Another important feature of the retractor is allow insertion of retractor blades without damage to the tissue. To achieve this the lumbar spinal fusion retractor and distractor system of the above mentioned application is constructed to displace only a small volume when inserted in the incision before it is opened, or "spread" to provide a clear view of the operating field.

Another important feature of the retractor is that it stay in position in the difficult lumbar fusion. To prevent such occurrences, fixation screws are provided that pass through blades of the retractor and are fastened to adjacent vertebra.

However, another common problem with this retractor is that no single length of blade that is suitable for all patients. Therefore several different size blades must be provided for different patients. This requires up to at least twelve different blades being provided and sterilized for an operation. The size and length of the blades can vary anywhere from 10 cm to 24 cm. Also when the retractor is placed in the patient, the surgeon may have to experiment with different length blades until he gets the right length. This increases the length of the operation and the danger of increased trauma to the patient. It would be advantageous if a single blade could be used having a length adjustment allowing rapid positioning and placement.

Another important aspect of the retractor is the provision of viewing an extremely small area during this surgical procedure to minimize the size of the incision. Thus it is apparent that a very clear view of the operating site must be provided. To accomplish this light pipes are used on the end of long cables that provide intense lumination of the surgical site. Since the volume of the area being operated on is small, the inclusion of a light pipe in the patient creates additional problems of interference with the surgical procedure.

It would therefore be advantageous if a method could be provided to accommodate a light pipe and providing intense lumination while avoiding interference with the surgical procedure.

It is therefore one object of the present invention to provided an improved retractor having retractor blades that are adjustable in length.

Still another object of the present invention is to provide a retractor with an adjustable length blades that remain fixed at an adjusted position.

Still another object of the present invention is to provide a retractor having an adjustable length blades having guides for fixation screws for attaching the retractor to the vertebrae of the patient.

Still another object of the present invention is to provide a retractor having adjustable length retractor blades with stops to prevent the adjustable length blades from being dislodged from the retractor.

Yet another object of the present invention is to provide a retractor having adjustable length retractor blades that are held in place at their adjusted position by frictionally engaging leaf springs.

Yet another object of the present invention is to provide adjustable length adjustable blades having a guide for receiving and holding a light pipe.

Yet another object of the present invention is to provide a retractor having adjustable length blades with guides for attaching multiple fixation screws to vertebra.

Other objects and advantages of the invention will become more apparent from the following portion of this specification, and the accompanying drawings.

BRIEF DESCRIPTION OF THE INVENTION

The purpose of the prevent invention is to provide an improved retractor such as a lumbar fusion laminectomy retractor and distractor that has adjustable length blades and guides for accommodating a plurality of fixation screws and a light pipe.

The lumbar fusion retractor and distractor of the present invention is comprised of a retractor frame each having a stationary arm on the end of the crossbar having a rack gear and a movable arm that includes a crank mechanism. For a lumbar fusions a retractor frame and a distractor frame are provided. The movable arm on each of the frames is adjustable along the rack gear along the crossbar by a crank mechanism disclosed and described in U.S. Pat. No. 5,167,223 issued Dec. 1, 1996 to T. Koros et al and incorporated herein by reference.

The movable arm is movable along the rack gear of the crossbar for fine adjustment by the crank mechanism comprised of a pinion gear engaging the rack gear turned by a foldable crank handle that closes and opens the parallel arms. The retractor and distractor frames, with folded crank arms, provide a low profile to minimize interference with the surgeon performing the surgical procedure.

For lumbar fusion surgical procedures a pair of retractor frames known as a retractor and distractor are provided. The distractor includes fixation screws to allow adjacent vertebrae to be spread by the distractor. With two retractor frames (i.e., a retractor and distractor) the retractor blades surround the surgical site providing a clear view to the surgeon. With the retractor/distractor disclosed in U.S. patent application Ser. No. 08/935,761 (pending) disclosed hereinabove the blades are first positioned in the incision around the surgical site and with a clamp handle the clamps on each retractor blade to manual insert and position of the blade. Depending upon the patient's anatomy several different length blades may be tried before the appropriate length is selected. Two of the blades are attached to adjacent vertebrae by fixation screws. The retractor and distractor frames then engage the blades and are retracted by operating the crank mechanisms to spread the retractor and the incision to provide a clear view of the surgical site. The non-fixed blades may be tilted to provide a wider field of view as described in the prior application referred to hereinabove.

The present invention avoids the need for up to 12 or more different blades by providing variable length blades. While the variable length blades of the invention are described with respect to the retractor/distractor system for lumbar fusions, they of course can be attached to any retractor for use in any abdominal surgery.

The variable length retractor blades are comprised of a blade having flanges or edges on either side providing channels for receiving a telescoping blade extension. The variable length blade is thus comprised of two pieces; an upper fixed length portion having channels for receiving a lower adjustable portion or extension which telescopes into the upper portion. Thus a single blade can cover a wide range of depths from about 10 cm to about 18 cm. For longer blades up to 24 cm. a second variable length blade will be provided. A single blades can cover a nominal depth of up to 24 or 25 cm. would have a closed length of approximately 14 to 15 cm. To cover depths of less than 14 cm. a second variable length blade can be provided that would cover a range of 10 to about 18 cm.

The telescoping extension on the variable length retractor blades has a slightly curved shaped and it includes stops at the upper end of the extension to prevent the lower portion from becoming detached. An optional but preferred feature is inclusion of frictionally engaging integrally formed leaf springs that frictionally press against the telescoping extension to hold it at whatever position it may be set. The blade itself and the extension are substantially smooth somewhat curved shaped similar to standard blades.

In another optional but preferred embodiment the blades include tubular guides for fixation screws and a light pipe. In this embodiment the tubular guides are formed in the upper and the lower ends of the variable retractor blade extension. Preferably there are three tubular guides allowing attachment by a pair of fixation screws and a third tubular bore or guide for receiving a light pipe.

The retractor/distractor frame disclosed and described in U.S. patent application Ser. No. 08/935,761 (pending) filed Sep. 23, 1997 discloses a blade having a single centrally located channel slot for receiving a single fixation screw. However it has been discovered that additional fixation screws are preferred to provide added stability. For that reason the variable length extendible blade of the present invention provides at least two tubular guides for fixation screws that can be spaced apart approximately the width of the blade. A third tubular guide is provided for receiving and holding a light pipe to illuminate the surgical site.

As in the prior application referred to hereinabove the lumbar retractor/distractor system is carefully positioned by first placing the variable length blades in the incision on opposite sides of the spine, chosen according to patient's requirement. With the extendible blades the length of the blade can be adjusted to the depth required. The longer variable length would be extendible from approximately 14 to 15 cm. to up to 24 or 25 cm. If a shorter blade is needed a second pair of extendible blades can be provided. Thus the present invention reduces the number of blades that must be kept available from at least twelve to no more than four and possibly only two. The blades are positioned by clamping a handle on a retractor blade having a boss or header for receiving clamp. This allows the blade to be manually inserted in the incision and positioned adjacent to surgical site.

After the hand retraction by manually placing the variable length blades the retractor frames are introduced with the blades properly positioned, or placed in a standard mid-line incision. The retractor frames are comprised of a crossbar, having a rack gear and a pair of arms attached to the crossbar. One retractor arm is stationary at the end of the crossbar while the other arm is movable to open or close the retractor arms to spread the incision.

The retractor arms are positioned fully closed between the heads of the retractor blades and cranked open until the extendible blades become engaged with notches or slots in the end of the retractor arms. The retractor arms are then opened until the desired retraction is achieved and a clear view of the operating site is obtained. The heads of the blades self-engage and self-lock in the slots at the end of the retractor arms and are held firmly in place by tissue pressure. The clamp handle used to manually positioning the blades may then be removed.

With a clear view of the operating site by the position of the variable length retractor blades and open retractor arms spreading the incision a distractor at right angles to the retractor can be introduced. The variable length distractor blades having tubular guides for fixation screws are carefully placed in the incision in the cephalat-ciudad direction with clamp handles as before. Instead of a single screw in the invention described in the patent application referred to hereinabove, a pair of screws can be slid down the pair of tubular guides and then screwed into adjacent vertebrae on opposite sides of the diseased lumbar disc. Usually pilot holes will be drilled in the vertebrae to ease the insertion of the fixation screws.

A third tubular channel between the outer tubular channels is provided to receive a right angle light pipe that provides intense illumination of the surgical site. Once the variable length blades are positioned and pinned in place by the fixation screws the second offset frame can be introduced to engage the heads of the variable length distractor blades. The adjacent vertebrae can then be gently spread by cranking the right angle offset distractor frame to spread the firmly attached distractor.

If the variable length blades are used with the retractor frame of the patent application described hereinabove the field of view can be widened by using the tilt mechanism to spread the tips of the blades to retract the surrounding tissue without enlarging the incision. When in this final position the surgeon has now a clear, lighted view of the lumbar disc region. The sequence of installing retractor and distractor blades and frames, of course, may vary. Further the variable length retractable blades shown and described in this application can be used with other retractor frames that have conventional retractor arms for receiving the heads of the blades.

The above and other novel features of the invention will be more fully understood from the following detailed description and the accompanying drawings, in which:

BRIEF DESCRIPTION OF THE DRAWINGS

FIG. 2 is a perspective view of a plain variable length retractor blade having a telescoping extension.

FIG. 3 is a perspective view of a second embodiment of a retractor variable length blade including tubular guides for mounting a plurality of fixation screws and a light pipe.

FIG. 5 is a sectional view of the retractor/distractor system with the variable length blade taken at 5—5 of FIG. 4.

FIG. 6 is a partial sectional view taken at 6 of FIG. 5 illustrating the adjustment restraining system for the variable length blade telescoping extension.

DETAILED DESCRIPTION OF THE INVENTION

Figure 1:
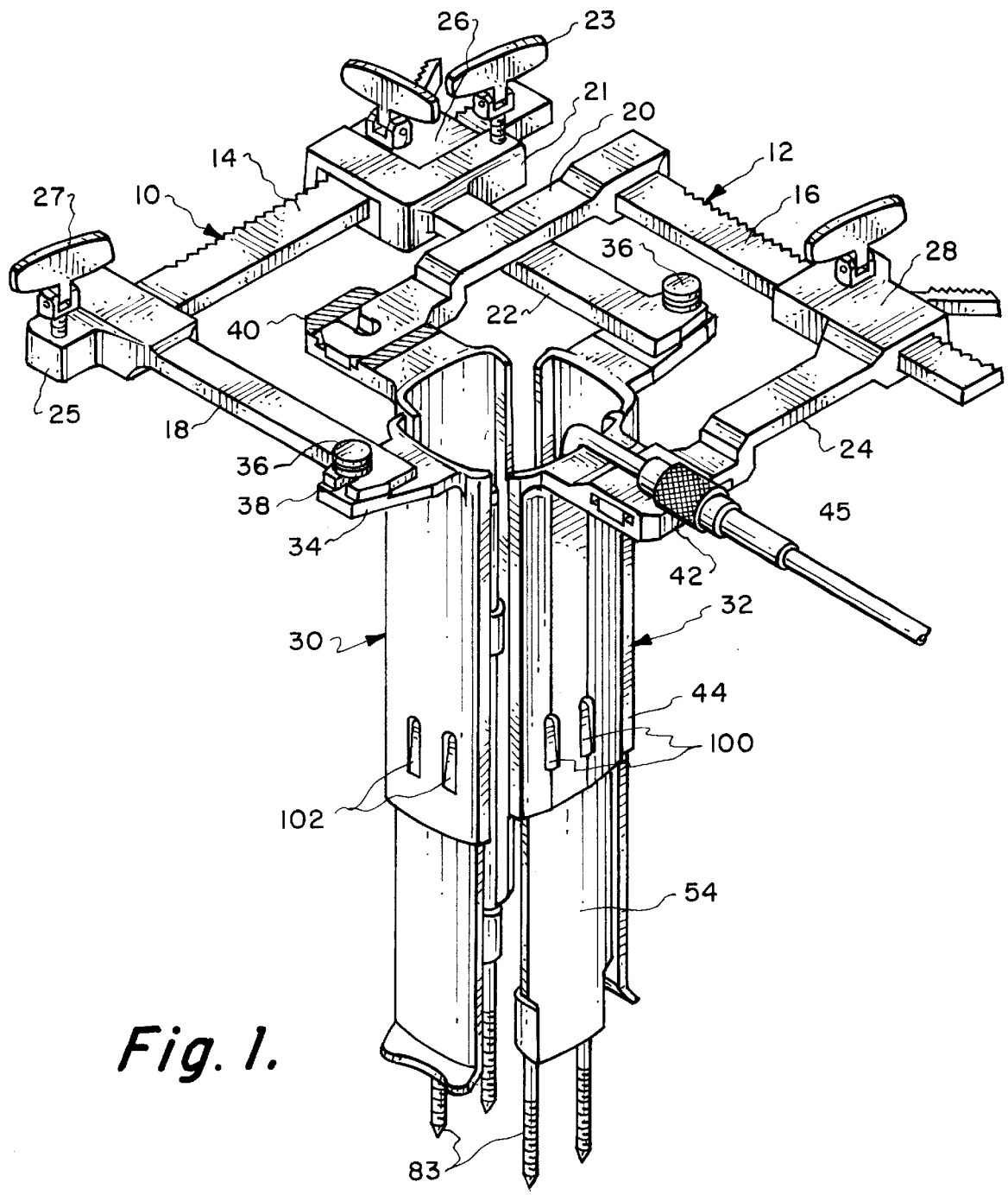
FIG. 1 is an isometric view of a retractor/distractor system using variable length telescoping blades according to the invention.

A retractor/distractor system similar to that shown and described in U.S. patent application Ser. No. 08/935,761 (pending) filed Sep. 23, 1997 by T. Koros et al is shown in generally in FIG. 1. The retractor/distractor system is comprised of a retractor 10 and a distractor 12 each comprised of frames 14 and 16 respectively having stationary arms 18 and 20 and movable arms 22 and 24. Movable arms 22 and 24 are movable by crank mechanisms 26 and 28 as described in the above identified application incorporated herein by reference. Also included in this application is the tilt mechanism for tilting the non-fixed retractor blades described in the above-identified application.

An improvement to the retractor/distractor system is provided by variable length retractor blades 30 and variable length distractor blades 32. Variable length retractor blades 30 have a flange 34 with a boss or head 36 that engages a slot 38 in stationary arm 18 and movable arm 22. Likewise distractor variable length blades have flanges 40 and 42 with slots for receiving the ends of stationary arm 20 and movable arm 24.

The versatility of the retractor/distractor system is improved by the variable length telescoping blades which reduce the number of blades used for this system to no more than four. The variable length retractor/distractor blades 30 and 32 are shown in greater detail in FIGS. 2 and 3. Variable length retractor blade 30 has a flange 34 with a header or boss 36 for engagement by arms of the retractor after placement by a clamp handle (not shown). Previously retractor blades varying in length from 10 cm. up to about 25 cm. in at least four different sizes were required. The result is that for retractor 10 at least eight blades had to be sterilized and prepared for each operation. With improvement of the present invention one or at most two variable length retractor blades 30 are sufficient.

Variable length retractor blade 30 is comprised of an upper fixed retractor blade 44 having flanges 46 and 48 channels 50 and 52 for slidably receiving telescoping blade extension 54. Blade extension 54 is retracted or extended by sliding it downward or upward in channels 50 and 52. Stops are provided by studs 56 on each side of the blade that abut shoulders 58 formed on flanges 46 and 48. This prevents blade extension 54 from sliding out of fixed blade 44. The end of blade extension 54 has the usual curled end 60 to assist in holding tissue away from the surgical site.

Two sizes of variable length retractor blades should be sufficient to cover the range necessary. One size would be in a range of from about 10 to 12 cm. in a retracted position to about 18 cm. in an extended position. The total range of coverage would be from about 10 cm to about 25 cm. A second variable length blade would have a retracted length of approximately 14 to 15 cm. and an extended length of up to 24 to 25 cm. Thus variable length retractor blades for the retractor used in the lumbar fusion retractor/distractor system in FIG. 1 would be no more than four.

Variable length distractor blade 32 for use with fixation screws is illustrated in FIG. 3. Variable length distractor blade 32 has flange 42 having socket 43 for receiving the end of the fixed distractor arm 20 and movable distractor arm 24 as described previously. Variable length distractor blade 32 is comprised of fixed upper portion 62 and telescoping blade extension 64. Fixed blade portion 62 has flanges 66 and 68 forming channels 70 and 72 for receiving telescoping blade extension 64. The lower portion of flanges 66 and 68 are provided with shoulders 74 and 76 for engaging stops or studs 78 and 80 on the upper end of the blade extension 64 to prevent the blade from slipping out of fixed portion 62.

Distractor blades for use in lumbar fusion described in the patent application referred to hereinabove include a channel or slot for receiving a single fixation screw. However it has been discovered that additional fixation screws would be advantageous to provide stability and improve support for the distractor system. Thus telescoping blade extension 64 of the present variable length blade 32 is provided with tubular guides 82 at the top of blade extension 64 and aligned tubular guides 86 at the bottom end of variable extension 64.

The outermost guides of tubular guides 82 and 86 can support a pair of fixation screws 83 for each variable length distractor blade. The third or center tubular guide can be used to support a light pipe 45 providing intense illumination to the surgical site without interfering with the surgical procedure.

Figure 4:
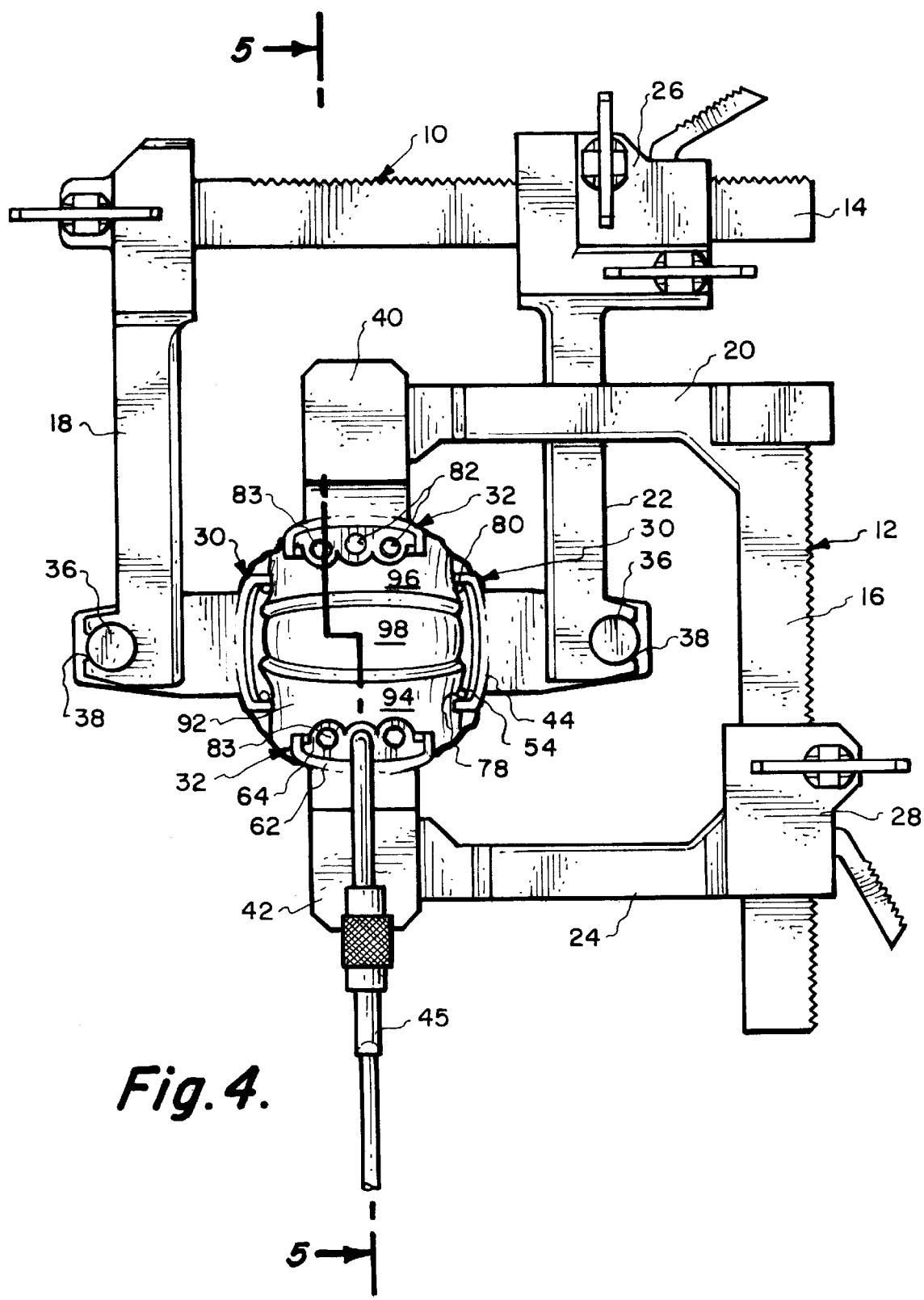
FIG. 4 is a top view of the retractor/distractor system placed in an incision for a clear view of the surgical site.

The installation and operation of the invention is illustrated in FIGS. 4 through 6. Variable length retractor blades 30 are carefully placed in an incision by a clamp handle traverse to spine 92. Telescoping blade extension 54 may then be adjusted to a length sufficient to retract the tissue adjacent to each side of spine 92. Retractor frame 10, in a fully closed position, is then placed between retractor blade heads 36 and opened by operating crank mechanism 26 until notches 38 engage the end of the retractor blades. The clamp handle may then be removed and retractor 10 opened further by turning the crank handle until the desired retraction of the incision is obtained.

Offset distractor frame 12 is then positioned in the incision with fixation screws 83 screwed into vertebrae 94 and 96 of spine 92 on opposite sides of affected disc 98. Fixation screws 83 firmly hold offset retractor frame in position allowing adjacent vertebrae 94 and 96 to be spread providing a clear view of the operating site.

The visibility of the operating site is substantially improved by a light pipe 45 inserted in tubular guide 82 as shown in FIG. 5. Light pipe 45 bends at a 90° angle over flange 42 of variable length distractor blade 32 and engaged tubular guide 82 between the tubular guides holding fixation screws 83. As described previously two fixation screws 83 are inserted through tubular guides 82 at the upper and lower end of variable length blade extension 64 and screwed into adjacent disc 94 and 96. Pilot holes may be drilled in each disc 94 and 96 for placement of fixation screws. Light pipe 45 is then placed in tubular guide 82 between fixation screws 83 in one of the adjustable length distractor blades 32. Light emitted from end 47 of light pipe 45 provides intense, clear illumination of the disc 98 being operated on.

Each telescoping extension in variable length retractor/distractor blades 30 and 32 is firmly held in an adjusted position by an integrally formed leaf spring 100 illustrated in the partial sectional view of FIG. 6. Leaf spring 100 is integrally formed in the upper fixed portion 62 of variable distractor blade 32 and presses firmly against blade extension 64 holding it in its adjusted position by friction. Preferably there are two such leaf springs in each variable distractor blade 32 and similar leaf springs 102 in variable length retractor blade 30.

With the distractor in place as illustrated in FIGS. 4 and 5 distractor arms 20 and 24 may be spread by operating crank mechanism 28 to spread vertebrae 94 and 96. This permits the surgeon to efficiently operate on affected disc 98.

The retractor/distractor system with variable length adjustable blades 30 and 32 also includes the tilt mechanism disclosed and described in U.S. patent application Ser. No. 08/935,761 (pending) referred to hereinabove and incorporated by reference. After placement of the retractor/distractor in the incision the field of view can be improved by tilting non-fixed variable length retractor blades 30 by operating tilt mechanisms 21 and 25. Tilt mechanisms 21 and 25 are adjusted by operating tilt crank handles 23 and 27 as described in the above identified application. The use of variable length adjustable blades in combination with the tilt mechanism substantially increases the versatility of the retractor/distractor system.

Thus there has been described a unique, novel variable length retractor/distractor blade that reduce the number of blades necessary for surgical procedures. Variable length retractor blades are disclosed having an adjustable telescoping extension slidably mounted in a fixed upper portion of the retractor blade that is held in adjustable position by integrally formed leaf springs. A conventional flange and header on the blade is provided for placement by a clamp and engagement by ends of retractor arms. Similar distractor blades are disclosed having an adjustable telescoping extension that include tubular guides for fixation screws as well as an additional guide for receiving a light pipe to intensely illuminate a surgical site. While the variable length retractor and distractor blades are described for use with a lumbar fusion retractor/distractor system they obviously may be used for other surgical procedures and are constructed with flanges that will fit other conventional retractor arms. The variable length retractor/distractor blades of the present invention provide a unique feature of minimizing the number of blades needed for a particular surgical procedure from twelve or more down to about four.

This invention is not to be limited by the embodiment shown in the drawings and described in the description which is given by way of example and not of limitation, but only in accordance with the scope of the appended claims.

What is claimed is:

1. A variable length blade for a surgical retractor comprising;
   a fixed blade having longitudinal flanges forming channels;
   means for securing said fixed blade to a retractor arm;
   an extendible blade, said extendible blade telescopically engaging said channels on said fixed blade;
   blade restraining means for restraining and holding said extendible blade in an adjusted position, said blade restraining means comprising frictionally engaging means on said fixed blade for frictionally engaging said telescoping extendible blade in an adjusted position;
   whereby said variable length retractor blade can be adjusted for use on a wide range of patients.

2. The variable length blade according to claim 1 in which said frictionally engaging means comprises leaf springs integrally formed on said fixed blade to hold said telescoping extendible blade in an adjusted position.

3. The variable length blade according to claim 2 including means for preventing said telescopically extendible blade from disengaging from said fixed blade.

4. The variable length blade according to claim 3 in which said means for preventing said extendible blade from disengaging comprises; stop means on said extendible blade.

5. The variable length blade according to claim 4 in which said stop means comprises; at least one stud on said extendible blade.

6. The variable length blade according to claim 5 in which said at least one stud comprises a pair of studs.

7. The variable length blade according to claim 6 in which said stop means includes; terminating means terminating said channels in said longitudinal flanges.

8. The variable length blade according to claim 7 in which said terminating means comprises a shoulder formed on said longitudinal flanges; said pair of studs engaging said shoulders.

9. The variable length blade according to claim 8 including at least two tubular guides formed on a face of said telescopically extendible blade for receiving one or more fixation screws.

10. The variable length blade according to claim 9 in which said at least two tubular guides comprise three tubular guides for receiving two fixation screws and a light pipe.

11. The variable length blade according to claim 10 in which said tubular guides are in groups of three at an upper end and a lower end of said telescopically extendible blade.

12. The variable length blade according to claim 11 including at least two tubular guides formed on a face of said telescopically extendible blade for receiving one or more fixation screws.

13. The variable length blade according to claim 12 in which said at least two tubular guides comprise three tubular guides for receiving two fixation screws and a light pipe.

14. The variable length blade according to claim 13 in which said tubular guides are in groups of three at an upper end and a lower end of said telescopically extendible blade.

15. A lumbar spinal fusion retractor and distractor system comprising;
   a retractor frame having parallel arms extending perpendicular to a crossbar, one of said arms being movable toward or away from the other;
   a pair of variable length retractor blades engaging free ends of said pair of parallel arms for spreading and retracting a surgical incision;
   a distractor frame having parallel arms extending perpendicular to a crossbar, one of said parallel arms being movable toward or away from the other;
   a pair of distractor variable length blades engaging free ends of said parallel arms;
   fastening means for fastening said pair of distractor blades to adjacent vertebra;
   whereby said distractor frame and pair of distractor blades are firmly held in place on a spinal column to provide a clear view and distraction of an operating site.

16. The system according to claim 15 in which said variable length retractor and distractor blades comprise;

a fixed blade;

means for securing said fixed blade to a retractor arm;

an extendible blade, said extendible blade telescopically engaging said fixed blade;

blade restraining means for restraining and holding said extendible blade in an adjusted position;

whereby said variable length retractor blade can be adjusted for use on a wide range of patients.

17. The system according to claim 16 in which said fixed blade has longitudinal flanges forming channels; said telescopically extendible blade slidably engaging said longitudinal channels for telescopic retraction into or extension from said fixed blade to adjustably vary the overall length of said variable length blade according to the size of the patient.

18. The system according to claim 17 in which said blade restraining means comprises; frictionally engaging leaf springs integrally formed in said fixed blade to hold said telescopically extendible blade in an adjusted position.

19. The system according to claim 18 in which said variable length blades on said distractor include at least two tubular guides formed on a face of said telescopically extendible blade for receiving one or more fixation screws.

20. The system according to claim 19 in which said at least two tubular guides comprise three tubular guides for receiving two fixation screws and a light pipe.

21. The variable length blade according to claim 21 in which said tubular guides are in groups of three at an upper end and a lower end of said extendible blade.

22. The system according to claim 15 including means for spreading tips on said pair of variable length retractor blades after placement in an incision and engagement with said arms on said retractor frame.

23. The system according to claim 22 in which said means for spreading tips of said pair of variable length retractor blades comprises means for tilting said pair of variable length retractor blades.

24. The system according to claim 23 in which said means for tilting said pair of variable length retractor blades comprises means for tilting said parallel arms with said variable length retractor blades engaged.

25. The system according to claim 24 in which said means for tilting said parallel arms comprises: coupling means coupling said parallel arms to said crossbar; angle adjusting means for adjusting the angle of said parallel arms with respect to said crossbar.

26. The system according to claim 25 in which said angle adjusting means comprises: a threaded shaft passing through said coupling on each of said parallel arms; a handle on an end of said threaded shaft; whereby rotation of said handles causes said coupling to tilt thereby tilting the respective parallel arm and variable length retractor blade.

* * * * *